(12) United States Patent
Sharma et al.

(10) Patent No.: US 7,884,229 B2
(45) Date of Patent: Feb. 8, 2011

(54) METHOD FOR MAKING A POLYETHER MONOMER

(75) Inventors: Amit K. Sharma, Burlington, NJ (US); Claude K. Martin, East Windsor, NJ (US); Aziz Boukhelifa, North Brunswick, NJ (US); Ning Chen, Plainsboro, NJ (US)

(73) Assignee: Rhodia Inc., Cranbury, NJ (US)

( * ) Notice: Subject to any disclaimer, the term of this patent is extended or adjusted under 35 U.S.C. 154(b) by 1748 days.

(21) Appl. No.: 10/838,714

(22) Filed: May 4, 2004

(65) Prior Publication Data

US 2004/0260116 A1    Dec. 23, 2004

Related U.S. Application Data

(60) Provisional application No. 60/479,522, filed on Jun. 17, 2003.

(51) Int. Cl.
*C07C 67/26* (2006.01)
*C07C 69/52* (2006.01)

(52) U.S. Cl. ........................ 560/209; 560/224

(58) Field of Classification Search .............. 560/209, 560/224

See application file for complete search history.

(56) References Cited

U.S. PATENT DOCUMENTS

| | | | |
|---|---|---|---|
| 3,708,524 A | 1/1973 | Murayama et al. | 260/186 B |
| 4,376,723 A * | 3/1983 | Wolfe et al. | 502/152 |
| 5,322,960 A | 6/1994 | Sakamoto et al. | 560/205 |
| 5,834,576 A * | 11/1998 | Nagano et al. | 526/318.3 |
| 6,624,286 B2 | 9/2003 | Hofmann et al. | 528/415 |

* cited by examiner

*Primary Examiner*—Taylor Victor Oh

(57) ABSTRACT

A method for making a polyether monomer having at least one unsaturated site per molecule and having a desired number of alkoxyl repeating units includes the steps of reacting an active hydrogen-containing monomer having at least one unsaturated site per molecule with an alkyl oxide in the presence of an alkoxylation catalyst and a polymerization inhibitor at a temperature from about 30° C. to less than 45° C. to produce a polyether monomer. In one embodiment, from about 5 to about 1000 parts by weight of a phenothiazine polymerization inhibitor per one million parts by weight of the active hydrogen-containing monomer phenothiazine compound is used as the polymerization inhibitor.

20 Claims, No Drawings

METHOD FOR MAKING A POLYETHER MONOMER

This application claims the benefit of U.S. Provisional Application No. 60/479,522, filed Jun. 17, 2003.

FIELD OF THE INVENTION

This invention relates to a method for making a polyether monomer, more particularly to method for making a polyether monomer that provides improved inhibition of undesired polymerization of the polyether monomer product.

BACKGROUND OF THE INVENTION

The acid-catalyzed reaction of an alkyl oxide, for example, ethylene oxide, with a monomer having an active hydrogen atom and a site of unsaturation, such as hydroxyalkyl methacrylate, to form a polyether monomer, for example, a polyethoxylated methacrylate, is know. Such reactions are typically catalyzed by Lewis acids, such as $FeCl_3$. The polyether monomer products formed in such reactions may undesirably polymerize to form a gel. Typically, a phenolic polymerization inhibitor, such as p-methoxy phenol, is used to inhibit the undesired polymerization of the polyether monomer product.

The use of phenolic polymerization inhibitors has not provided a completely satisfactory solution to the problem of undesired polymerization. It is desirable to minimize or eliminate the presence of $O_2$ in the reaction vessel, since the presence of $O_2$ and alkylene oxide in the reactor may create potentially explosive conditions. However, p-methoxy phenol is ineffective as a polymerization inhibitor in the absence of air. This dilemma is typically addressed by conducting the alkoxylation reaction with some oxygen present in an attempt to balance the two competing concerns. Further, p-methoxy phenol contains an active hydrogen atom, and may therefore react with the alkyl oxide under the reaction conditions. In practice it is typically necessary to add a large amount of amount of p-methoxy phenol to offset its undesired consumption during the reaction.

SUMMARY OF THE INVENTION

In a first aspect, the present invention is directed to a method for making polyether monomer having at least one unsaturated site per molecule and having a desired number of alkoxyl repeating units per molecule, comprising reacting an active hydrogen-containing monomer having at least one unsaturated site per molecule with an alkyl oxide in the presence of an alkoxylation catalyst and a polymerization inhibitor at a temperature from about 30° C. to less than 45° C. to produce the polyether monomer.

In a second aspect, the present invention is directed to a method for making a stabilized polyether monomer having least one unsaturated site per molecule and having a desired number of alkoxyl repeating units per molecule, comprising reacting an active hydrogen-containing monomer having at least one unsaturated site per molecule with an alkyl oxide in the presence of an alkoxylation catalyst and from about 5 to about 1000 parts by weight of a phenothiazine polymerization inhibitor per one million parts by weight of the active hydrogen-containing monomer to produce the polyether monomer.

In a third aspect, the present invention is directed to a stabilized polyether monomer composition, comprising:

the polyether monomer, said polyether monomer having at least one unsaturated site per molecule and having a desired number of alkoxyl repeating units per molecule, and an effective amount of a phenothiazine polymerization inhibitor.

DETAILED DESCRIPTION OF INVENTION AND PREFERRED EMBODIMENTS

The present method is directed to synthesis of a poly(oxyalkylene)ester according to the general reaction scheme:

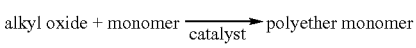

Typically, the active hydrogen-containing monomer, alkoxylation catalyst, and a polymerization inhibitor are charged to a reactor and a stream of alkyl oxide, in a relative amount that is appropriate to obtain for the desired degree of alkoxylation of the active hydrogen-containing monomer, is then fed to the reactor.

The alkoxylation reaction is carried out by contacting appropriate relative amounts of the alkyl oxide and active hydrogen-containing monomer in the reactor in the presence of a catalytically effective amount of the alkoxylation catalyst and a polymerization inhibitor at a gage pressure of from about 20 pounds per square inch ("psig") to about 50 psig, more typically, from about 18 psig to about 48 psig, and a temperature of from 30° C. to about 60° C. The contacting is carried out until the alkoxylation reaction reaches a desired degree of completion, typically for a time period of about 2 hours to about 10 hours, more typically from about 4 hours to about 5 hours.

Once the alkoxylation reaction is complete, the polyether monomer product is stripped to remove volatile components.

Suitable alkyl oxides are compounds according to formula (1):

(1)

wherein $R^1$ is H or $(C_1-C_4)$alkyl.

As used herein the term "alkyl" means a straight or branched saturated aliphatic group and use of the terminology (Cx-Cy), wherein x and y are each positive integers, in reference to a substituent group indicates that the substituent group contains from x carbon atoms per group to y carbon atoms per group.

Suitable $(C_1-C_4)$alkyl groups include methyl, ethyl, n-propyl, iso-propyl n-butyl, sec-butyl and tert-butyl.

Suitable alkyl oxides include, for example, ethylene oxide, propylene oxide, butylene oxide, pentylene oxide, hexylene oxide. In one embodiment, the alkyl oxide is selected from ethylene oxide and propylene oxide.

Suitable active hydrogen-containing monomers are those compounds having at least one active hydrogen atom per molecule and having at least one unsaturated site, typically an α,β-unsaturated site, per molecule, such as for example, hydroyalkyl acrylates, hydroxyalkyl methacrylates, allyl alcohol, 2-allyl phenol, acrylic acid, methacrylic acid, itaconic acid, crotonic acid, maleic acid, fumaric acid. As used herein, the term "active hydrogen" means that the hydrogen atom is susceptible to removal under the relevant reaction conditions to leave an electron rich nucleophilic species. Functional groups that contain a suitable active hydrogen atom include hydroxyl, carboxyl, thio, primary amino, and secondary amino. The unsaturated site of the monomer does not participate in the alkoxylation reaction and is thus available for subsequent reaction.

In one embodiment, the active hydrogen-containing monomer comprises a compound according to according to formula (2):

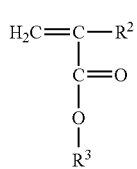

(2)

wherein:

$R^2$ is H or $(C_1-C_6)$alkyl, and $R^3$ is H, hydroxy$(C_1-C_6)$alkyl, thio$(C_1-C_6)$alkyl, or amino $(C_1-C_6)$alkyl.

Suitable $(C_1-C_6)$alkyl groups include methyl, ethyl, n-propyl, iso-propyl n-butyl, sec-butyl and tert-butyl, n-pentyl and n-hexyl. Suitable hydroxy$(C_1-C_6)$alkyl groups include hydroxymethyl, hydroxyethyl, hydroxypropyl, hydroxybutyl, hydroxypentyl and hydroxyhexyl. Suitable thio$(C_1-C_6)$ alkyl groups include thioethyl, thiopropyl, thiobutyl, and thiohexyl. Suitable amino$(C_1-C_6)$alkyl groups include aminoethyl, aminopropyl, aminobutyl, and aminohexyl.

Suitable active hydrogen-containing monomers according to formula (2) include, for example, acrylic acid, methacrylic acid, hydroxyethyl acrylate, hydroxyethyl methacrylate, hydroxypropyl acrylate, hydroxypropyl methacrylate, hydroxybutyl acrylate, hydroxybutyl methacrylate, hydroxypentyl acrylate, hydroxypentyl methacrylate, hydroxyhexyl acrylate, and hydroxyhexyl methacrylate.

In one embodiment, the active hydrogen-containing monomer comprises a monomer selected from hydroxyethyl acrylate, hydroxyethyl methacrylate, hydroxypropyl acrylate, and hydroxypropyl methacrylate, more typically, from hydroxyethyl methacrylate and hydroxypropyl methacrylate.

Suitable alkoxylation catalysts are those effective in catalyzing alkoxylation of the active hydrogen-containing monomer under relatively mild reaction conditions and include common acids, Lewis acids, zeolites, and ion exchange resins.

In one embodiment, the alkoxylation catalyst is a Lewis acid selected from $BF_3$, $AlCl_3$, and $FeCl_3$.

The alkoxylation catalyst is present in the alkoxylation reaction mixture in an amount effective to catalyze the alkoxylation reaction, typically in amount of from about 400 to about 1000 parts by weigh per one million parts by weight of alkoxylated product.

Suitable polymerization inhibitors are known compounds, such a free-radical scavengers, that inhibit polymerization of the active hydrogen-containing monomer and inhibit polymerization of the polyether monomer and include phenol compounds such as hydroquinone and p-methoxy phenol, phenothiazine compounds, such as phenothiazine, N-oxyl compounds such as di-tert-butyl nitroxide and 2,2,6,6 tetramethyl-4-hydroxypiperidiooxyl, and 2,2,5,5-tetramethyl-3-oxypiperidinooxyl.

The active hydrogen-containing monomer typically contains a polymerization inhibitor. Additional polymerization inhibitor is typically added to the active hydrogen-containing monomer prior to the alkoxylation reaction to inhibit undesired polymerization of the active hydrogen-containing monomer that could occur via reaction of the unsaturated sites of that monomer during the alkoxylation reaction and to inhibit undesired polymerization of the polyether monomer that could occur during storage via reaction of the unsaturated sites of that monomer.

The phenothiazine polymerization inhibitor comprises phenothiazine or a phenothiazine derivative that inhibits reaction of the unsaturated site of the polyether monomer to thereby inhibit undesired polymerization of such monomers.

In one embodiment, the phenothiazine inhibitor comprises at least one compound according to the formula (3):

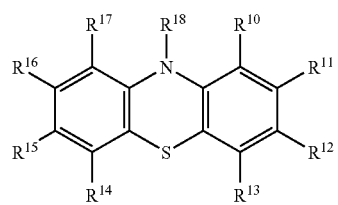

(3)

wherein:

$R^{10}$, $R^{11}$, $R^{12}$, $R^{13}$, $R^{14}$, $R^{15}$, $R^{16}$ and $R^{17}$ are each independently H, $(C^1-C_{12})$alkyl, aryl, alkaryl, aralkyl or halo, and $R^{18}$ is H or $(C_1-C_{12})$alkyl.

As used herein "aryl" means a single-ring aromatic group, such as phenyl, "alkaryl" means an alkyl substituted aryl group, such as tolyl or xylyl, "aralkyl" means an aryl substituted alkyl group such as phenylmethyl or phenylethyl, and "halo" means fluroro, chloro, bromo, or iodo.

Suitable $(C_1-C_{12})$alkyl groups include methyl, ethyl, n-propyl, iso-propyl n-butyl, sec-butyl and tert-butyl, pentyl and hexyl, heptyl, octyl, nonyl, decyl, undecyl, and dodecyl.

Suitable phenothiazine inhibitors include phenothiazine, bis-(α-methylbenzyl)phenothiazine, 3,7-dioctylphenothiazine, and bis-(α-dimethylbenzyl)phenothiazine.

The polyether monomer product is the polyalkoxylated product of reaction of the alkyl oxide with the active hydrogen-containing monomer. The polyether monomer contains at least one polyalkoxyl substituent per molecule, that is, in place of the active hydrogen of the active hydrogen-containing monomer, and contains one unsaturated site per molecule.

In one embodiment, the polyether monomer contains from 2 to 100, more typically from 2 to 50, and still more typically from 2 to 25, alkoxyl units per molecule.

In one embodiment, the polyether monomer contains from 5 to 100, more typically from 5 to 50, and still more typically from 5 to 25, alkoxyl units per molecule.

The alkoxyl units may be the same or different from each other. If the polyalkoxyl substituent of the polyether monomer comprises two or more different types of alkoxyl units, for example, ethoxide and propoxide units, then such units may be may arranged in random order, in alternating order or in blocks.

In one embodiment, the polyether monomer product is a compound according to the formula (4):

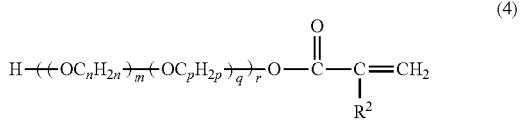

(4)

wherein:

R² is defined as above, n and p are each independently integers of from 1 to 6, m is independently an integer from 1 to 100, provided that each m is independent if r is greater than 1, q is 0 or q is an integer from 1-100, provided that each q is independent if r is greater than 1, r is an integer of from 1 to 50, provided that r is 1 if q is 0, and the product r(m+q) is an integer of from 2 to 100.

In one embodiment, n and p are each independently 2, 3, or 4.

In one embodiment, m is an integer from 2 to 100, more typically from 2 to 50, and still more typically from 2 to 25. In another embodiment, the m is an integer from 5 to 100, more typically from 5 to 50, and still more typically from 5 to 25.

In one embodiment, r is 1 and the sum of m+q is an integer from 2 to 100, more typically from 2 to 50, and still more typically from 2 to 25. In another embodiment, r is 1 and the sum of m+q is an integer from 5 to 100, more typically from 5 to 50, and still more typically from 5 to 25.

In one embodiment, the polyether monomer comprises a polyethoxyl acrylic ester, polyethoxyl methacrylic ester, a polypropoxyl acrylic ester, polypropoxyl methacrylic ester or a mixture thereof.

In one embodiment, the alkoxylation reaction is carried out by contacting the alkyl oxide and active hydrogen-containing monomer are contacted in the reactor in the presence of the polymerization inhibitor and a catalytically effective amount of the alkoxylation catalyst at a temperature of from 45° C. to about 60° C., more typically from 45° C. to about 55° C.

In another embodiment, the alkoxylation reaction is carried out by contacting the alkyl oxide and active hydrogen-containing monomer are contacted in the reactor in the presence of the polymerization inhibitor and a catalytically effective amount of the alkoxylation catalyst at a temperature of from about 30° C. to less than 45° C.

In general, lowering the reaction temperature is undesirable in the sense that the lower temperature results in a lower rate of reaction. In an extreme case, too lowering the reaction temperature too aggressively may stall the reaction, in which case a dangerous buildup of alkyl oxide may occur in the reactor. Typically, the alkoxylation reaction is run in the temperature range of from about 45° C. to about 60° C. in order avoid any risk of stalling the reaction.

However, it has been found that carrying out the alkoxylation reaction at a temperature in the range of from about 30° C. to less than 45° C. provides an acceptable rate of reaction and provides improved product quality, as evidenced by the relatively low viscosity of polyether monomer product made at a temperature within the range of about 30° C. to less than 45° C. range, compared to polyether monomer product made at a temperature within the range of from 45° C. to about 60° C. It is believed that carrying out the alkoxylation reaction within the temperature range of about 30° C. to less than 45° C. discourages formation of undesired higher molecular weight by-products and that the corresponding reduced amount of such by-products in the polyether monomer made within such temperature range accounts for the lower viscosity of such polyether monomer product.

In one embodiment, alkoxylation of the active hydrogen-containing monomer is conducted in the presence of from about 5 to about 1000 parts by weight of a phenothiazine inhibitor per one million parts by weight active hydrogen-containing monomer. In another embodiment, alkoxylation of the active hydrogen-containing monomer is conducted in the presence of from about 8 to about 250 parts by weight of a phenothiazine inhibitor per one million parts by weight active hydrogen-containing monomer. Use in the alkoxylation reaction mixture of an amount of phenothiazine polymerization inhibitor within the above described ranges provides a phenothiazine polymerization inhibitor content in the polyether monomer product that is effective to inhibit polymerization of the polyether monomer product, typically a phenothiazine content of from 5 to 800, more typically from about 5 to about 300, parts by weight phenothiazine polymerization inhibitor per one million parts by weight of the polyether monomer.

In one embodiment, the alkoxylation method is conducted in a substantially inert, more preferably, inert, atmosphere using a phenothiazine polymerization inhibitor. Alkyl oxides may undergo explosive decomposition in the presence of oxygen. As used herein, the terminology "inert atmosphere" means that the reactor headspace is purged with an inert gas, typically, nitrogen, prior to introduction of the alkyl oxide and the alkoxylation reaction is conducted in the presence of the inert gas under conditions effective to render the alkyl oxide non-decomposable. Substantially no, or, more preferably, no $O_2$ is present in such inert atmosphere. Phenolic inhibitors typically require the presence of oxygen to function effectively as polymerization inhibitors. In contrast, phenothiazine inhibitors are effective as polymerization inhibitors in the absence of oxygen. Use of a phenothiazine inhibitor as a polymerization inhibitor allows the alkoxylation reaction to be conducted in an inert atmosphere.

In one embodiment, less than 1000 parts by weight p-methoxy phenol is added to the alkoxylation reaction mixture per one million parts by weight active hydrogen-containing monomer, preferably substantially no p-methoxy phenol is added to the alkoxylation mixture. Preferably, the p-methoxy phenol content of the polyether monomer is less than about 1000, more preferably less than 500, even more preferably less than 100, and still more preferably less than 50 parts by weight p-methoxy phenol per one million parts by weight polyether monomer.

In a preferred embodiment wherein a Lewis acid alkoxylation catalyst is used, the alkoxylation catalyst is neutralized with a base soon after the alkoxylation reaction is completed. The presence of non-neutralized Lewis acid catalyst was found to interfere with the ability of the phenothiazine inhibitor to inhibit polymerization of the polyether monomer product. Suitable bases for neutralizing the alkoxylation catalyst include weak bases, such as, for example, sodium carbonate or sodium bicarbonate.

EXAMPLES 1-4

The polyether monomer composition of Example 1 was made as follows. About 190 g of hydroxyethyl methacrylate was charged to a clean Paar reactor. This was followed by the addition of 0.015 g phenothiazine to give about 18 parts by weight phenothiazine per one million parts by weight hydroxyethyl methacrylate. About 0.43 g (0.05%) of 50% $BF_3$/etherate solution was then added as an alkoxylation catalyst. About 640-650 g of ethylene oxide gas was introduced to the reactor and was reacted with the hydroxyethyl methacrylate at a temperature from 48° C. to 52° C. for a time period of about 5 hours to provide a final polyether monomer product mass of about 764 g. The final polyether monomer product was immediately treated with about 80 to 100 g of 20% $Na_2CO_3$ solution in water to neutralize the $BF_3$ catalyst.

The polyether monomer composition of Example 2 was made in a manner directly analogous to that of Example 1, except that 0.08 g phenothiazine was added to the reactor to give about 106 parts by weight phenothiazine per one million parts by weight hydroxyethyl methacrylate and the reaction was conducted at a temperature of from 37° C. to 44° C.

The polyether monomer composition of Example 3 was made in a manner directly analogous to that of Example 1, except that 0.2 g of phenothiazine was added to the reactor to give about 228 parts by weight phenothiazine per one million parts by weight hydroxyethyl methacrylate.

The polyether monomer composition of Example 4 was made by adding 1000 parts by weight p-methoxy phenol per one million parts by weight polyether monomer to the sample of Example 1.

The polyether monomer compositions of Examples 1-4 were each initially free flowing liquids. Samples of the polyether monomer compositions of Examples 1-4 were stored in a refrigerator at 4° C. The polyether monomer compositions of Examples 1, 2, and 3 remained free flowing after 24 hours at 4° C. The polyether monomer composition of Example 4 polymerized within 30 minutes at 4° C.

The viscosities of samples of the respective polyether monomer compositions of Examples 1 and 4 were measured using a Brookfield viscometer (# 31 spindle at 50 rpm) and were each found to exhibit a viscosity of 77 centipoise (cp). Each of the samples were then held at 60° C. The sample of the polyether monomer composition of Example 4 polymerized within one week at 60° C. The room temperature viscosity of the polyether monomer composition of Example 1 remained unchanged at its initial value of 77 cp after 6 weeks of storage at 60° C.

In each case, the polyether monomer composition Example 4, which included both p-methoxy phenol and phenothiazine as polymerization inhibitors, showed a marked decrease in stability compared to the polyether monomer composition of Example 1, which contained only phenothiazine as a polymerization inhibitor.

The viscosity of the polyether monomer compositions of Examples 2 and 3 were each measured at each of several different temperatures using a Brookfield viscometer (using either a #18 spindle at 50 rpm centipoise or a #31 spindle at 50 rpm for viscosities, depending on the viscosity range). Result are given below in TABLE I, as viscosity, in centipoise (cp), versus temperature, in degrees Centigrade (° C.).

TABLE I

| Example 2 | | Example 3 | |
| --- | --- | --- | --- |
| Temperature (° C.) | Viscosity (cp) | Temperature (° C.) | Viscosity (cp) |
| 9.5 | 50 | 9.6 | 128 |
| — | — | 13.5 | 123 |
| 14 | 42.4 | 14.9 | 114 |
| 19.2 | 33 | 19.6 | 94 |
| — | — | 22.3 | 83 |
| 23.5 | 28.5 | 24.1 | 74 |
| 26 | 25.3 | 26.5 | 68 |
| 28 | 23.6 | 29.1 | 60 |
| 34 | 19.4 | — | — |
| 34.7 | 18.4 | 39.4 | 33 |

TABLE I-continued

| Example 2 | | Example 3 | |
| --- | --- | --- | --- |
| Temperature (° C.) | Viscosity (cp) | Temperature (° C.) | Viscosity (cp) |
| 40.3 | 15.2 | 40.1 | 31.4 |
| 45 | 13.4 | 44 | 27.6 |
| 47 | 12.7 | 48 | 24.2 |
| 49.5 | 12 | 49.9 | 22.3 |
| — | — | 53.4 | 20.2 |
| 54.8 | 10.3 | 55 | 19 |

The viscosity of polyether monomer composition Example 6 was higher than that of polyether monomer composition Example 5. The difference in viscosity was most dramatic at lower temperatures, where the respective viscosities were found to differ by a factor of greater than 2.

The invention claimed is:

1. A method for making a polyether monomer having at least one unsaturated site per molecule and having a desired number of alkoxyl repeating units per molecule, comprising reacting in the absence of oxygen an active hydrogen-containing monomer having at least one unsaturated site per molecule with an alkyl oxide in the presence of an alkoxylation catalyst and a phenothiazine polymerization inhibitor at a temperature from about 30° C. to less than 45° C. to produce the polyether monomer.

2. The method of claim 1, wherein the alkylene oxide is one or more of ethylene oxide and propylene oxide.

3. The method of claim 1, wherein the active hydrogen-containing monomer is one or more of hydroxyethyl acrylate, hydroxypropyl acrylate, hydroxyethyl methacrylate, and hydroxypropyl methacrylate.

4. The method of claim 1 wherein the phenothiazine polymerization inhibitor is phenothiazine.

5. The method of claim 1 wherein the phenothiazine polymerization inhibitor is present in an amount of from about 5 to about 1000 parts by weight per one million parts by weight of the active hydrogen-containing monomer.

6. A method for making a polyalkoxylated acrylic or methacrylic ester, comprising reacting one or more of hydroxyethyl acrylate, hydroxypropyl acrylate, hydroxyethyl methacrylate and hydroxypropyl methacrylate with one or more of ethylene oxide and propylene oxide in the presence of an alkoxylation catalyst and a polymerization inhibitor at a temperature from about 30° C. to less than 45° C.

7. A method for making a stabilized polyether monomer having at least one unsaturated site per molecule and having a desired number of alkoxyl repeating units per molecule, comprising:
    reacting an active hydrogen-containing monomer having at least one unsaturated site per molecule with an alkyl oxide in the presence of an alkoxylation catalyst and from about 5 to about 1000 parts by weight of a phenothiazine polymerization inhibitor per one million parts by weight of the active hydrogen-containing monomer to produce the polyether monomer.

8. The method of claim 7, wherein the alkylene oxide is one or more of ethylene oxide and propylene oxide.

9. The method of claim 7, wherein the active hydrogen-containing monomer is one or more of hydroxyethyl acrylate, hydroxypropyl acrylate, hydroxyethyl methacrylate, hydroxypropyl methacrylate.

10. The method of claim 7, wherein the phenothiazine polymerization inhibitor is phenothiazine.

11. The method of claim 7, wherein less than 1000 parts by weight p-methoxy phenol per one million parts by weight active hydrogen-containing monomer is added to the active hydrogen-containing monomer, alkyl oxide, alkoxylation catalyst, and phenothiazine polymerization inhibitor.

12. A method for making a polyalkoxylated acrylic or methacrylic ester, comprising reacting one or more of hydroxyethyl acrylate, hydroxypropyl acrylate, hydroxyethyl methacrylate, and hydroxypropyl methacrylate with one or more of ethylene oxide and propylene oxide in a substantially inert atmosphere in the substantial absence of oxygen and in the presence of an alkoxylation catalyst and from about 5 to about 1000 parts by weight of a phenothiazine polymerization inhibitor per one million parts by weight of the hydroxyethyl acrylate, hydroxypropyl acrylate, hydroxyethyl methacrylate, and hydroxypropyl methacrylate.

13. A stabilized polyether monomer composition prepared by the method of claim 1, comprising:
    a polyether monomer, said polyether monomer having at least one unsaturated site per molecule and having a desired number of alkoxyl repeating units per molecule, and
    an effective amount of a phenothiazine polymerization inhibitor.

14. The composition of claim 13, wherein the polyether monomer is one or more of a polyethoxyl acrylic ester, a polyethoxyl methacrylic ester, a polypropoxyl acrylic ester, and a polypropoxyl methacrylic ester.

15. The composition of claim 13, wherein the phenothiazine polymerization inhibitor is phenothiazine.

16. The composition of claim 13, wherein the composition comprises about 5 to about 300 parts by weight of a phenothiazine polymerization inhibitor per one million parts by weight of the polyether monomer.

17. The polyether monomer of claim 13, wherein the p-methoxy phenol content of the polyether monomer is less than about 1000 parts by weight p-methoxy phenol per one million parts by weight polyether monomer.

18. A stabilized polyether monomer composition prepared by the method of claim 1, comprising:
    one or more of a polyethoxyl acrylic ester, a polyethoxyl methacrylic ester, a polypropoxyl acrylic ester, and a polypropoxyl methacrylic ester, and
    from about 5 to about 300 parts by weight of a phenothiazine polymerization inhibitor per one million parts by weight of the polyether monomer.

19. A method for making a polyether monomer having at least one unsaturated site per molecule and having a desired number of alkoxyl repeating units per molecule, consisting essentially of reacting in the absence of oxygen an active hydrogen-containing monomer having at least one unsaturated site per molecule with an alkyl oxide in the presence of an alkoxylation catalyst and a phenothiazine polymerization inhibitor at a temperature from about 30° C. to less than 45° C. to produce the polyether monomer.

20. The method of claim 1 comprising conducting the reaction in the absence of solvent.

\* \* \* \* \*